(12) United States Patent
Bergstrom et al.

(10) Patent No.: US 6,896,883 B2
(45) Date of Patent: May 24, 2005

(54) **BIOCONTROL FOR PLANTS WITH *BACILLUS SUBTILIS, PSEUDOMONAS PUTIDA*, AND *SPOROBOLOMYCES ROSEUS***

(75) Inventors: Gary C. Bergstrom, Ithaca, NY (US); Wilmar Corio da Luz, Pass Fundo (BR)

(73) Assignees: Cornell Research Foundation, Inc., Ithaca, NY (US); Embrapa Trigo (BR)

( * ) Notice: Subject to any disclaimer, the term of this patent is extended or adjusted under 35 U.S.C. 154(b) by 60 days.

(21) Appl. No.: 10/241,252

(22) Filed: Sep. 10, 2002

(65) Prior Publication Data

US 2003/0082792 A1 May 1, 2003

Related U.S. Application Data

(63) Continuation-in-part of application No. 09/118,656, filed on Jul. 17, 1998, now abandoned.
(60) Provisional application No. 60/053,310, filed on Jul. 22, 1997.

(51) Int. Cl.$^7$ .......................... A01N 63/00; C12N 1/20; C12N 1/00
(52) U.S. Cl. .............................. 424/93.462; 424/93.46; 435/252.5; 435/839; 435/832
(58) Field of Search ........................ 424/93.462, 93.46; 435/252.5, 839, 832

(56) References Cited

U.S. PATENT DOCUMENTS

| | | |
|---|---|---|
| 4,447,539 A | 5/1984 | Pillis et al. |
| 4,584,274 A | 4/1986 | Suslow |
| 5,215,747 A * | 6/1993 | Hairston et al. ........ 424/93.462 |
| 5,270,059 A | 12/1993 | Janisiwicz et al. |
| 5,288,488 A | 2/1994 | Backman et al. |
| 5,326,701 A | 7/1994 | Shieh et al. |
| 5,503,652 A | 4/1996 | Kloepper et al. |
| 5,589,381 A | 12/1996 | Neyra et al. |
| 5,650,372 A * | 7/1997 | Branly et al. ................ 504/117 |
| 5,753,222 A * | 5/1998 | Marrone et al. ....... 424/93.462 |

OTHER PUBLICATIONS

Hofle, M.G., "Transfer RNAs as Genotypic Fingerprints of Eubacteria," *Arch. Microbiol.*, 153:299–304 (1990).

Porteous et al., "An Effective Method to Extract DNA from Environmental Samples for Polymerase Chain Reaction Amplification and DNA Fingerprint Analysis," *Current Microbiology*, 29:301–307 (1994).

Ospina–Giraldo et al., "In vitro Inhibition of *Trichodema-harzianum*, Cause of Mushroom Green Mold, by *Paenibacillus Macerans* Isolated From Compost," Ann. Meeting of the Amer. Phytopathological Soc., S82:736A (abstract only) (1996).

Bergey's Manual of Sytematic Bacteriology, Williams & Wilkins, vol. 2, pp. 1123–1124, 1126, 1133 (1986).

ATCC Bacteria and Bacteriophages Catalogue, ATCC, 19$^{th}$ Edition, pp. 258–259 (1996).

Ash et al., "Molecular Identification of rRNA Group 3 Using a PCR Probe Test," *Antoine van Leeuwnhoek* 64:253–260 (1993).

\* cited by examiner

*Primary Examiner*—Vera Afremova
(74) *Attorney, Agent, or Firm*—Nixon Peabody LLP (57) ABSTRACT

The present invention is directed to isolated *Bacillus subtilis, Pseudomonas putida*, and *Sporobolomyces roseus* which are useful as a biocontrol agent. These organisms are useful in a method of imparting to plants protection against plant pathogens by applying them to plants, plant seeds, or soil surrounding plants under conditions effective to impart disease protection to the plants or plants produced from the plant seeds. The biocontrol agents are also useful in a method of enhancing plant growth which involves applying them to plants, plants seeds, or soil surrounding plants under conditions effective to enhance growth in the plants or plants produced from the plant seeds.

33 Claims, 4 Drawing Sheets

BIOCONTROL FOR PLANTS WITH BACILLUS SUBTILIS, PSEUDOMONAS PUTIDA, AND SPOROBOLOMYCES ROSEUS

This application is a continuation-in-part of U.S. patent application Ser. No. 09/118,656, filed Jul. 17, 1998, now abandoned, which claims benefit of U.S. Provisional Patent Application Ser. No. 60/053,310, filed Jul. 22, 1997.

The present invention was made with support under USDA Hatch Project No. NYC153-472. The U.S. Government may have certain rights.

FIELD OF THE INVENTION

The present invention relates to biocontrol for plants with *Bacillus subtilis*, *Pseudomonas putida*, and *Sporobolomyces roseus*.

BACKGROUND OF THE INVENTION

There are approximately 40 biocontrol products commercially available for the control of plant diseases worldwide. Biocontrol products are available to control many diverse pathogens, as recently reviewed by Fravel, et al., "Availability and Application of Biocontrol Products," *Biological and Culture Tests for Control of Plant Diseases*, 11:1–7 (1996). At least 27 genera of fungi, 3 genera of bacteria, and 4 genera of nematodes are targeted for control by these products. More than half of these products control soilborne fungi. The biocontrol agents themselves are also diverse and include at least 9 genera of fungi, 4 genera of bacteria, and one actinomycete. Biocontrol products are used on a great variety of crops including greenhouse crops, row crops, field crops, perennial field crops, and trees and wood, as well as in special cropping systems such as mushroom cultivation. The products are applied in many ways. They may be sprayed onto plants or harvested fruits, drenched on harvested fruit or on plants, incorporated into the soil, applied as root dips, used to treat seeds, or inserted into trees or wood products. Biocontrol products currently on the market in the U.S. include Aspire, AQ-10, Galltrol A, Norbac 84C, Bio-Save 10, Bio-Save 11, Blightban A506, Victus, Epic, Kodiak, Deny, Mycostop, Binab-T and W, T-22G and T-22HB, and SoilGard.

Pathogens are controlled by biocontrol agents of the same species or genus as the pathogen in several cases. For example, nonpathogenic *Agrobacterium radiobacter* is used to control crown gall (Galltrol-A, Nogall, Diegall). Nonpathogenic *Fusarium oxysporum* is used to control *F. oxysporum* (Biofox C, Fusaclean) and *F. moniliforme* (Biofox C). Nonpathogenic *Pseudomonas solanacearum* controls pathogenic *P. solanacearum* (PSSOL), while *P. fluorescens* is used to control *P. tolassii* (Conquer, Victus). *Pythium oligandrum* is used to control *P. ultimum* (Polygandron). These agents may work through antibiosis (*A. radiobacter*; Kerr, A. "Biological Control of Crown Gall through Production of Agrocin 84," *Plant Dis.*, 64:25–30 (1980)), competition and induced systemic resistance (Fusaclean; Alabouvette, et al., "Recent Advances in the Biological Control of Fusarium Wilts," *Pestic. Sci.*, 37:365–373 (1993)), parasitism (Polygandron; Vesely, D. "Germinating Power of Oospores of *Pythium oligandrum* in a Powder Preparation," *Folia Microbiol.*, 32:502 (1987)).

Some biocontrol agents control only one pathogen. For example, Conquer and Victus both contain *P. fluorescens* used to control mushroom blotch caused by *P. tolassii*. Biocontrol agents are sometimes perceived as serving only niche markets since many products have narrow applicability. In part because of this perception, many biocontrol products are manufactured by small companies. However, most biocontrol agents have multiple pathogen and crop uses. For example, SoilGard controls damping-off incited by *Rhizoctonia solani* and *Pythium* spp. on bedding plants and vegetable transplants, as well as *Sclerotium rolfsii* on carrot and pepper in the field (Lumsden et al., "Biological Control of Damping-off Caused by *Pythium ultimum* and *Rhizoctonia solani* with *Gliocladium virens* in Soilless Mix," *Phytopathology*, 79:361–66 (1989); Ristaino et al., "Influence of Isolates of *Gliocladium virens* and Delivery Systems on Biological Control of Southern Blight on Carrot and Tomato in the Field," *Plant Dis.*, 78:153–56 (1994); Ristaino et al., "Soil Solarization and *Gliocladium virens* Reduce the Incidence of Southern Blight in Bell Pepper in the Field," *Phytopathology*, 84:1114 (1994)). Some products even control dissimilar pathogens. Deny controls *Rhizoctonia, Pythium, Fusarium,* as well as several nematodes. BlightBan A506 can be sprayed onto trees, strawberry, tomato, and potato plants to prevent frost damage and fire blight caused by *Erwinia amylovora*. *Trichoderma* spp. can control a wide variety of pathogens and appear in more products than any other microbe (Anti-Fungus; Binab T; Supresivit; T-22G and T-22HB; Trichopel, Trichoject, Trichodowels, and Trichoseal; TY). Products containing *Trichoderma* spp. control species of *Amillaria, Botrytis, Chondrostrenum, Colletotrichum, Fulvia, Fusarium, Monilia, Nectria, Phytophthora, Plasmopara, Pseudoperonospora, Pythium, Rhizoctonia, Rhizopus, Sclerotinia, Sclerotium, Verticillium,* and wood rot fungi.

Many biocontrol products are applied in agricultural environments of low ecological diversity in order to facilitate establishment of the biocontrol agent. For example, SoilGard and T-22G are mixed with soil-less potting mix. Similarly, Anti-Fungus is applied to soil following steaming or fumigation. Other biocontrol agents are used to protect plant parts. Galltrol-A, Nogall, Diegall, and Norbac 84C are all applied as root dips at transplant to prevent crown gall. Aspire, Bio-Save 10, and Bio-Save 11 are applied post-harvest to citrus or pome fruits to protect these fruits from post-harvest diseases. Several biocontrol agents, including Blue Circle, Epic, Kodiak, and T-22HB, are applied as seed treatments. Binab is applied by spraying, mixing with soil-less potting mix, painting on surfaces or inserting pellets into wood to control rot in wood and wood products. Mycostop is applied as a spray, drench, or through irrigation.

In order for biocontrol to be a useful component of an integrated pest management system, research is needed in several critical areas. This integrated approach will rely on accurate assessments of populations of pathogens present in an agricultural field and knowledge of economic thresholds for pathogen damage. Research needs to be aimed at an understanding of ecological parameters important for crop production and survival and efficacy of biocontrol agents, and at identifying and developing new biocontrol agents for control of plant diseases. Knowledge of the biology and ecology of the biocontrol agent, pathogen, and host plant can help to exploit strengths or weaknesses of these organisms to improve control performance. Similarly, knowledge of the ecological, biological, and physical conditions needed for successful biocontrol will permit optimization of these conditions to achieve the best possible levels of control.

The influence of the host plant on the composition and size of microbial communities has received little attention thus far. Larkin and coworkers (Larkin et al., "Ecology of *Fusarium oxysporum* f. sp. *Niveum* in Soils Suppressive and Conducive to Fusarium Wilt of Watermelon,"

Phytopathology, 83:1105–16 (1993); Larkin et al., "Effect of Successive Watermelon Plantings on *Fusarium oxysporum* and other Microorganisms in Soils Suppressive and Conducive to Fusarium Wilt of Watermelon," *Pathology*, (1993)) reported a cultivar-specific rhizosphere effect on soil and rhizosphere microbial communities associated with different watermelon cultivars. One cultivar in particular, Crimson Sweet, promoted the development of microorganisms antagonistic to the *Fusarium* wilt pathogen. More research is needed to determine the role of this type of interaction in the enhancement of biocontrol.

One barrier to acquiring an understanding of soil microbial systems has been the lack of suitable techniques for assaying soil samples. Population sizes of many soil microbes, especially fungi, are difficult to measure accurately for several reasons. The term "colony forming unit" reflects the fact that colonies arising on a plate may have come from, for example, microconidia, macroconidia, chlamydospores, ascospores, hyphal fragments, or other propagules. Further, the efficiency of recovery of propagules may differ from one soil to the next. In some cases, such as with *Fusarium* spp., the pathogens cannot be distinguished morphologically from the nonpathogens. In addition, many microbes are not easily cultured on standard media, although they may play significant roles in disease suppression, as with the mycoparsite *Sporidesmium sclerotivorum* for control of lettuce drop (Adams et al., "Economical Biological Control of Sclerotinia Lettuce Drop by *Sporidesmium sclerotivorum*," *Phytopathology*, 80:1120–24 (1990)). Finally, even when propagule numbers can be accurately estimated, the effectiveness of these propagules is dependent on their nutritional status and on the types and population sizes of other microbes present in the soil system. All of these shortcomings are compounded by the difficulty of sampling, particularly sampling of microsites. Research is needed to develop rapid, reliable, precise techniques for assaying soil microbial communities.

In the future, research should emphasize combinations of two or more biocontrol agents, since combinations may provide more consistent or more efficient control than a single biocontrol agent. For example, biocontrol agents with different optimal environmental conditions, or biocontrol agents with different mechanisms of action could be combined. Biocontrol agents may even act synergistically such as the combination of *Fusarium oxysporum* with *Pseudomonas* spp. to control *Fusarium* wilt (Lemanceau et al., "Biological Control of Fusarium Diseases by Fluorescent *Pseudomonas* and Non-pathogenic *Fusarium*," *Crop Prot.*, 10:279–86 (1991)). Research is also needed on combining biocontrol agents with other control methods. For example, sublethal heat (solarization) or pesticide stress may weaken a pathogen, making it more vulnerable to the action of biocontrol agents (Lifshitz et al., "The Effect of Sublethal Heating on Sclerotia of *Sclerotium rolfsii*," *Can. J. Microbiol.*, 29:1607–10 (1983); Tjamos, et al., "Detrimental Effects of Sublethal Heating and *Talaromyces flavus* on Microsclerotia of *Verticillium dahlias*," *Phytopathology*, 85:388–92 (1995)). Suitable systems also need to be developed for production, formulation and delivery of biocontrol agents, because these processes can greatly affect efficacy of the biocontrol agent.

Despite the existence and use of biocontrol agents in agriculture, there continues to be a need for development of new plant biocontrol agents. The present invention is directed to fulfilling this need.

SUMMARY OF THE INVENTION

The present invention is directed to isolated *Bacillus subtilis*, *Pseudomonas putida*, and *Sporobolomyces roseus* which are useful as biocontrol agents.

The present invention also relates to an isolated *Bacillus subtilis* that is useful as a biocontrol agent and which has a distinctive ribotype pattern as compared to other *Bacillus subtilis* isolates. In one embodiment, the *Bacillus subtilis* isolate has a ribotype pattern including the following peaks: (1) a first peak having a relative band intensity ("RBI") of between about 204 and 306 and an estimated molecular weight of between about 1.70 and 2.70 kilobase pairs (kb); (2) a second peak having an RBI of between about 168 and 252 and a molecular weight of between about 3.60 and 4.60 kb; (3) a third peak having an RBI of between about 72 and 108 and a molecular weight of between about 5.10 and 6.10 kb; (4) a fourth peak having an RBI of between about 116 and 174 and a molecular weight of between about 5.60 and 6.60 kb; (5) a fifth peak having an RBI of between about 116 and 174 and a molecular weight of between about 5.70 and 6.70 kb; (6) a sixth peak having an RBI of between about 84 and 126 and a molecular weight of between about 8.00 and 9.00 kb; and (7) a seventh peak having an RBI of between about 78 and 118 and a molecular weight of between about 11.00 and 12.17 kb, where the RBI was based on a value on a scale from 0 to 255.

The biocontrol agents are useful in a method of imparting to plants protection against plant pathogens. This method involves applying the biocontrol agent to plants, plant seeds, or soil surrounding plants under conditions effective to impart disease protection to plants or plants produced from the plant seeds.

The present invention is also directed to a method of enhancing plant growth. This involves applying the biocontrol agent to plants, plants seeds, or soil surrounding plants under conditions effective to enhance growth in the plants or plants produced from the plant seeds.

The present invention also relates to a supernatant obtained from a culture of either one of the *Bacillus subtilis*, *Pseudomonas putida*, or *Sporobolomyces roseus* biocontrol isolates, where the supernatant includes an antifungal metabolite produced by the respective biocontrol isolate.

The biocontrol agents of the present invention are highly useful in agriculture to protect plants from a variety of plant bacterial, fungal, and viral diseases. In addition, these agents can enhance the growth of treated plants. Significantly, these effects are achieved without being hazardous to animals or humans.

BRIEF DESCRIPTION OF THE DRAWINGS

FIGS. 1A–1C shows paired in-vito assays for antibiosis of *Fusarium graminearum* and *F. moniliforme* by the following candidate bioprotectants: FIG. 1A: *F. graminearum* with and without *Bacillus subtilis*; FIG. 1B: *F. moniliforme* with and without *Pseudomonas putida*; and FIG. 1C: *F. graminearum* with and without *Sporobolomyces roseus*.

DETAILED DESCRIPTION OF THE INVENTION

Figure 1A:
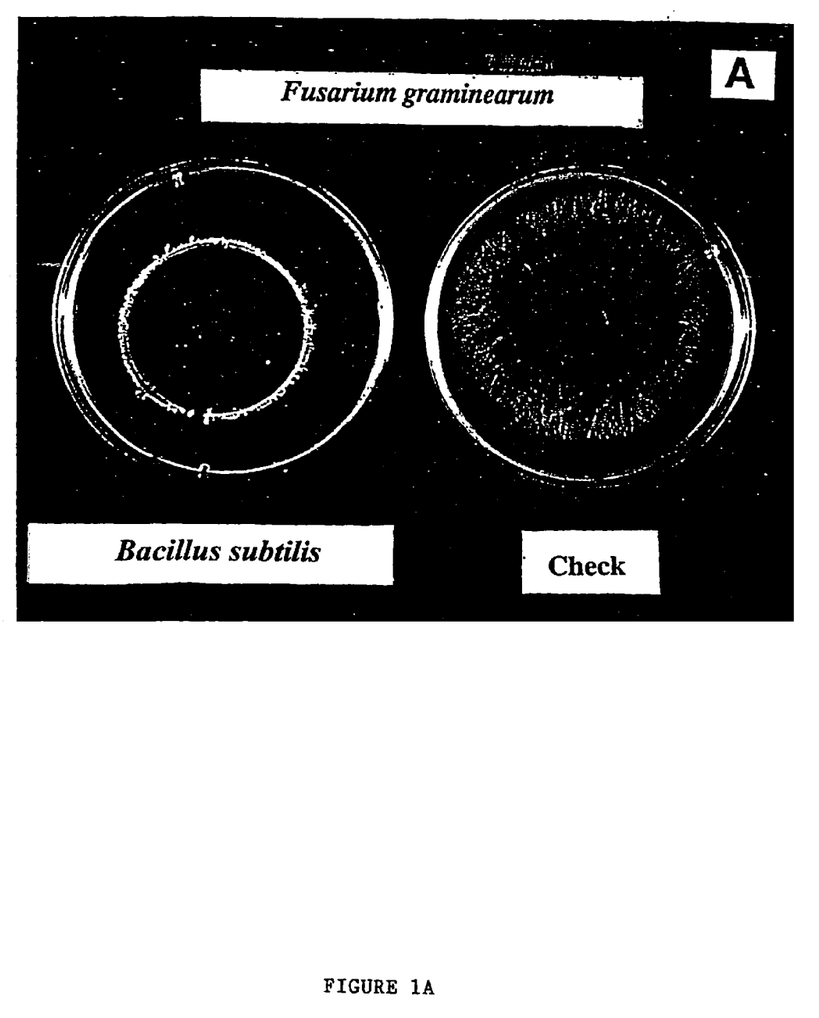
Figure 1B:
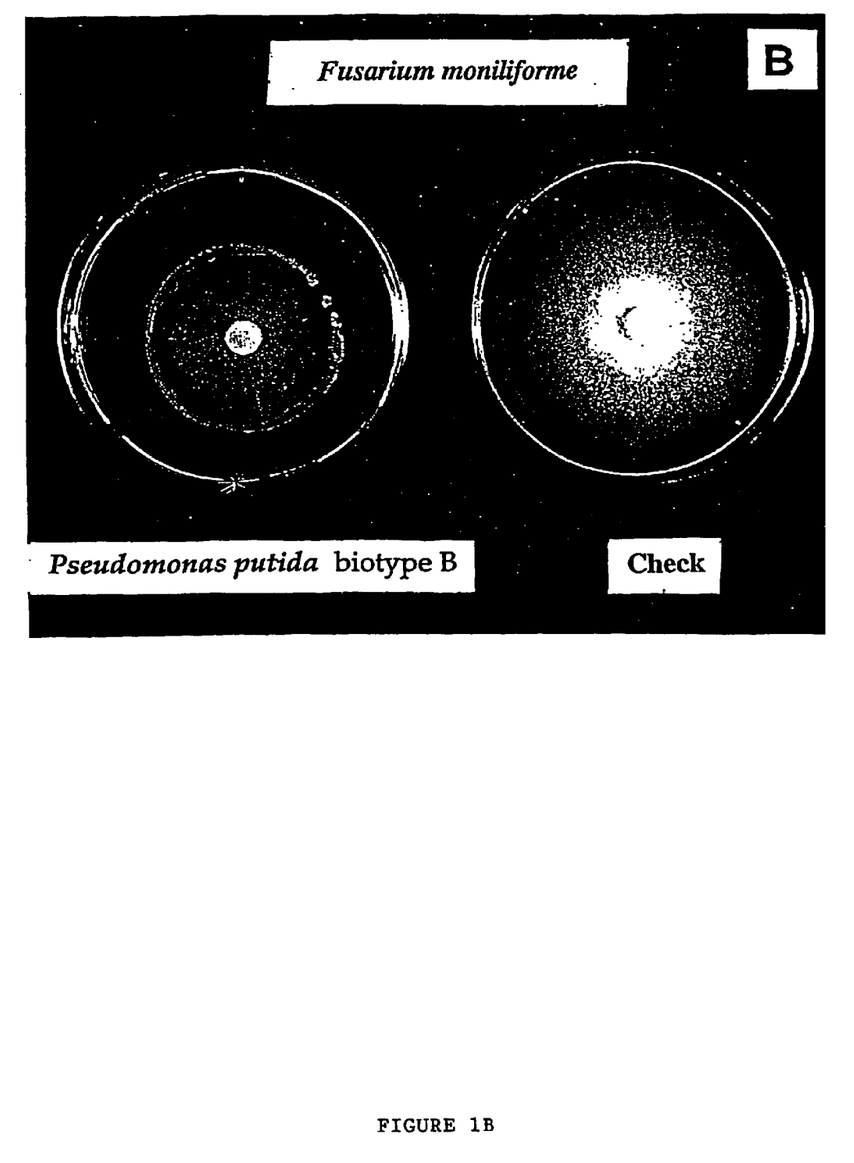
Figure 1C:
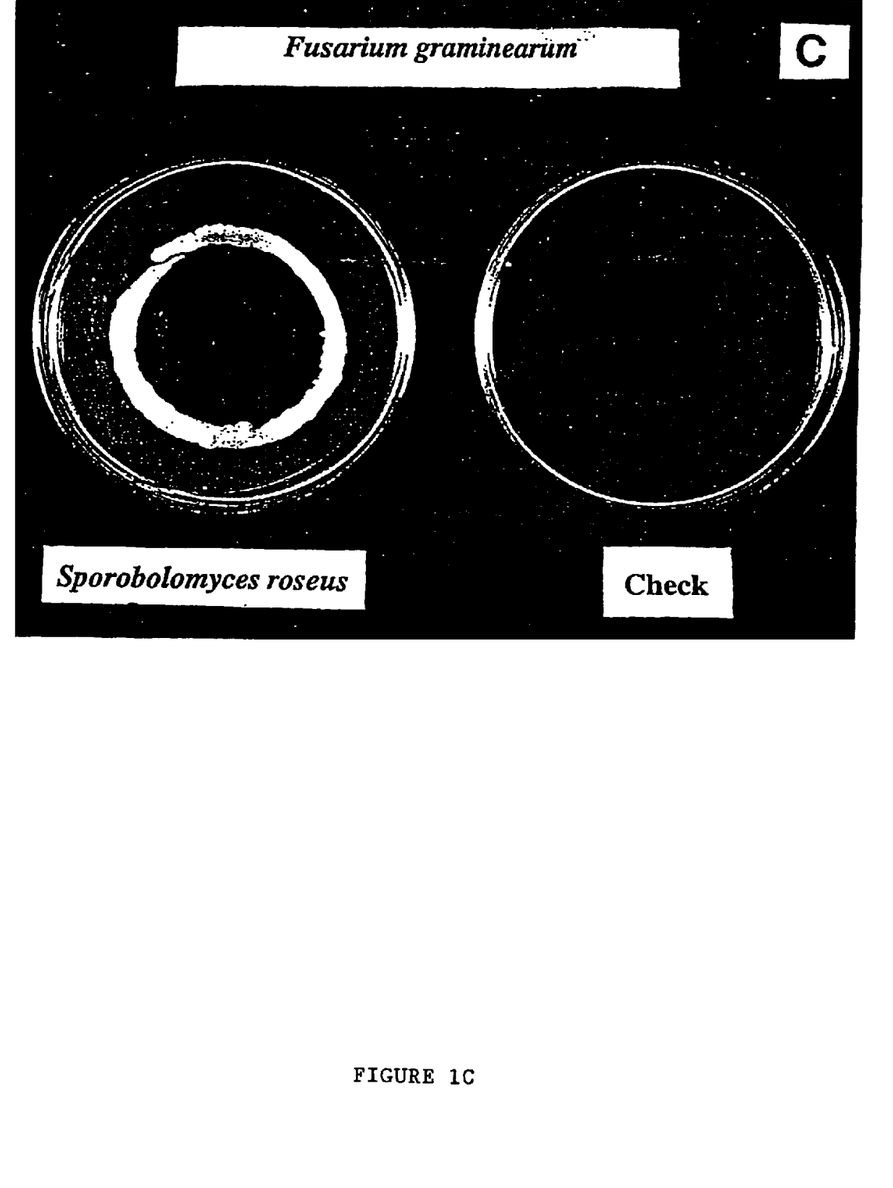
Figure 2:
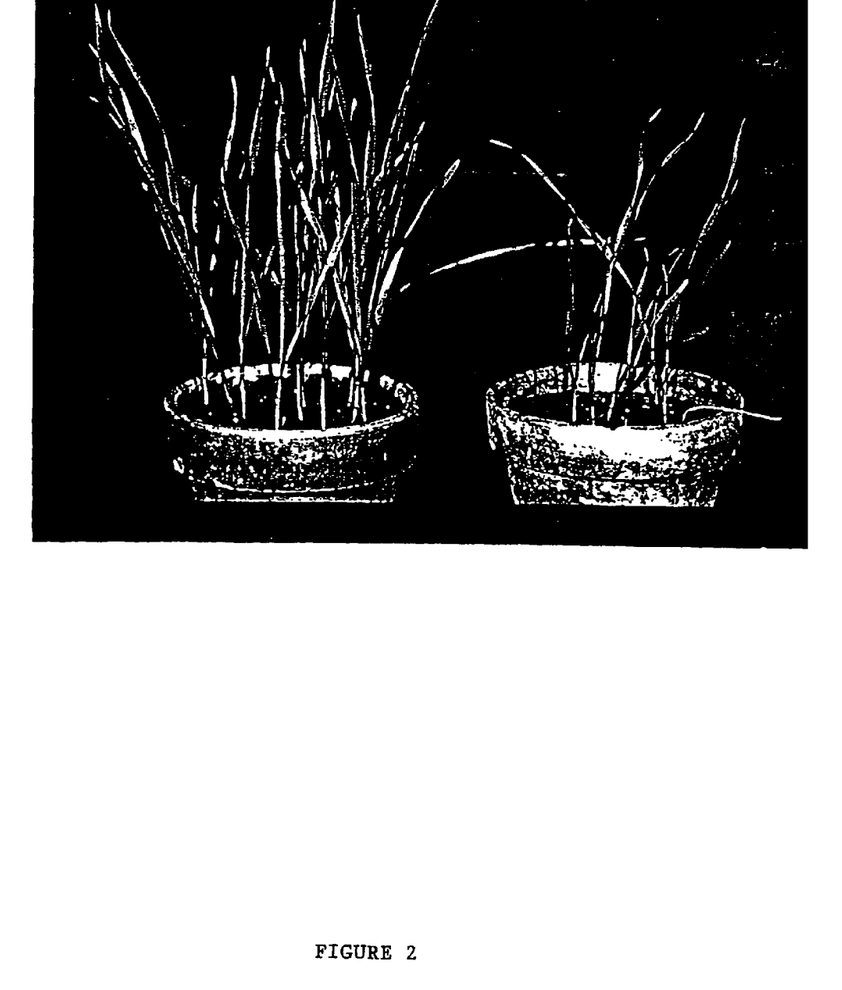
FIG. 2 shows wheat seeds naturally infected with *F. graminearum*. The plant on the right is grown from seed treated with *Bacillus subtilis*, while the plant on the left is grown from nontreated seed.

The present invention is directed to isolated *Bacillus subtilis*, *Pseudomonas putida*, and *Sporobolomyces roseus*, each of which are useful as biocontrol agent to impart disease protection to plants and to enhance plant growth. In one aspect of the present invention, the isolated biocontrol agent is in biologically pure form.

The *Bacillus subtilis* is a Gram variable rod, spore-forming bacteria. It is known as isolate 144 (and as "Trigo-Cor 1448") and has Embrapa Trigo Accession No. 144/88.4Lev, Cornell Accession No. Pma007BR-97, and ATCC Accession No. 202152 (deposit was made with American Type Culture Collection, 10801 University Boulevard, Manassas, Va. 20110-2209, on Jul. 8, 1998). This bacteria shows strong antibiosis against *Cochliobolus sativus* (spot blotch/common root rot of cereals), *Colletotrichum graminicola* (corn anthracnose), *Fusarium graminearum* (scab of cereals, ear/stalk rot of corn), *Fusarium moniliforme* (ear/stalk rot of corn), *Pyrenophora tritici-repentis* (tan spot of wheat), *Stagonospora nodorum* (*Stagonospora nodorum* blotch of wheat), *Stagonospora avenae* f. sp. *triticea* (*Stagonospora avenae* blotch of wheat), and *Stenocarpella maydis* (stalk/ear rot of corn). The *Bacillus subtilis* of the present invention shows excellent control of seed borne transmission of *Cochliobolus sativus, Pyrenophora tritici-riepentis*, and *Fusarium graminearum* in wheat and of *Fusarium moniliforme* in corn. It also prevents aerial inoculation of flowering wheat spikes with *Fusarium graminearum*, diminishes grain infection frequency by *Fusarium*, reduces grain weight reduction by *Fursarium*, and dramatically reduces grain contamination by *Fursarium* mycotoxin deoxynivalenol. In addition, this bacterium may be used to reduce contamination of grains and other plant products with harmful secondary fungal metabolites. The endophytic capability of this bacterium suggests additional applications for plant disease control. Seedlings and other plant propagative units can be inoculated for long-term plant protection.

The present invention also relates to an isolated *Bacillus subtilis* that is useful as a biocontrol agent and which has a distinctive ribotype pattern as compared to other *Bacillus subtilis* isolates, based on a ribotyping data compiled using a RiboPrinter® Microbial Characterization System (DuPont Qualicon, Wilmington, Del.). In one embodiment, the *Bacillus subtilis* isolate of the present invention has a ribotype pattern including the following peaks: (1) a first peak having a relative band intensity ("RBI") of between about 204 and 306 and an estimated molecular weight of between about 1.70 and 2.70 kilobase pairs (kb); (2) a second peak having an RBI of between about 168 and 252 and a molecular weight of between about 3.60 and 4.60 kb; (3) a third peak having an RBI of between about 72 and 108 and a molecular weight of between about 5.10 and 6.10 kb; (4) a fourth peak having an RBI of between about 116 and 174 and a molecular weight of between about 5.60 and 6.60 kb; (5) a fifth peak having an RBI of between about 116 and 174 and a molecular weight of between about 5.70 and 6.70 kb; (6) a sixth peak having an RBI of between about 84 and 126 and a molecular weight of between about 8.00 and 9.00 kb; and (7) a seventh peak having an RBI of between about 78 and 118 and a molecular weight of between about 11.00 and 12.17 kb, where the RBI was based on a value on a scale from 0 to 255.

In another embodiment, the ribotype pattern of the *Bacillus subtilis* isolate of the present invention has the following peaks: (1) a first peak having an RBI of approximately 255 and an estimated molecular weight of approximately 2.17 kb; (2) a second peak having an RBI of approximately 210 and a molecular weight of approximately 4.12 kb; (3) a third peak having an RBI of approximately 90 and a molecular weight of approximately 5.61 kb; (4) a fourth peak having an RBI of approximately 145 and a molecular weight of approximately 6.13 kb; (5) a fifth peak having an RBI of approximately 145 and a molecular weight of approximately 6.24 kb; (6) a sixth peak having an RBI of approximately 105 and a molecular weight of approximately 8.53 kb; and (7) a seventh peak having an RBI of approximately 98 and a molecular weight of approximately 11.59 kb.

The *Pseudomonas putida* is a Gram positive rod, non-spore forming bacteria. It is known as biotype B isolate 63 and has Embrapa Trigo Accession No. 63/88 4 B, Cornell Accession No. Ppu002BR-97, and ATCC Accession No. 202153 (deposit was made with American Type Culture Collection, 10801 University Boulevard, Manassas, Va. 20110-2209, on Jul. 8, 1998). This bacteria shows strong antibiosis against *Fusarium graminearum* and some antibiosis against *Cochliobolus sativus, Colletotrichum graminicola, Fusarium moiliforme, Stagonospora nodorum*, and *Stenocarpella maydis* (stalk/ear rot of corn). The *Pseudomonas putida* of the present invention is effective in controlling seedborne transmission of *Biopolaris sorokinianum* and *Fusarium graminearum* in wheat and of *Fusarium moniliforme* in corn. It also shows excellent control of soilborne *Fusarium graminearum* in corn, activity against aerial inoculation of flowering wheat spikes with *Fursarium*, and strongly reduces grain contamination by the *Fursarium* mycotoxin deoxynivalenol.

The *Sporobolomyces roseus* is a red pigment yeast. It is known as isolate 53 and has Embrapa Trigo Accession No. 53/94.535, Cornell Accession No. Sro001BR-97, and ATCC Accession No. 74456 (deposit was made with American Type Culture Collection, 10801 University Boulevard, Manassas, Va. 20110-2209, on Jul. 8, 1998). This biocontrol agent is useful against aerial inoculation of flowering spikes with *Fusarium graminearum*, diminishes grain infection frequency by *Fursarium*, and reduces grain contamination by the *Fursarium* mycotoxin deoxynivalenol. This is a strongly competitive organism in colonizing organic substrates and is a profuse sporulater. It can suppress the survival and sporulation of debris-borne plant pathogens on crop residue and thereby reduce disease in a subsequently planted crop, especially under conservation tillage agriculture.

The present invention also relates to a supernatant obtained from a culture of either one of the *Bacillus subtilis, Pseudomonas putida*, or *Sporobolomyces roseus* biocontrol isolates, where the supernatant includes an antifungal metabolite produced by the respective biocontrol isolate. As used in the present application, the term "supernatant" refers to the liquid suspension remaining when cells grown in a liquid medium (e.g., a liquid broth) are removed by centrifugation, filtration, sedimentation, or other means well known in the art. The term "metabolite" refers to any compound, substance or byproduct of a fermentation of the isolated biocontrol agents of the present invention that has antifungal activity.

The biocontrol agents of the present invention are useful in a method of imparting to plants protection against plant pathogens. This method involves applying the biocontrol agent to plants, plant seeds, or soil surrounding plants under conditions effective to impart disease protection to the plants and to plants produced from the plant seeds.

The method of imparting pathogen protection to plants in accordance with the present invention is useful in protecting plants against a wide variety of pathogens including viruses, bacteria, and fungi. Plants can be protected against, inter alia, the following fungi by use of the method of the present invention: *Fusarium oxysporum, Fusarium graminearum, Fusarium monilforme, Cochliobolus sativus, Collectotrichum graminicola, Stagonospora nodorum, Stagonospora avenae, Stenocarpella maydis*, and *Pyrenophora tritici-repentis*.

The present invention is also directed to a method of enhancing plant growth by applying the biocontrol agents of the present invention to plants, plant seeds, and soil surrounding plants under conditions effective to enhance growth of the plants or plants resulting from the treated seeds.

With regard to the use of the biocontrol agents of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

The methods of the present invention can be utilized to treat a wide variety of plants or their seeds to impart disease protection and/or to enhance growth. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

The methods of the present invention can be carried out through a variety of procedures when all or part of the plant is treated, including leaves, stems, roots, plant products (e.g., grain, fruit, forage, crop debris), propagules (e.g., cuttings), etc. Suitable application methods include high or low pressure spraying, drenching, and injection. When treating plant seeds, in accordance with the present invention, the biocontrol agent can be applied by low or high pressure spraying, coating, immersion, or injection. Biocontrol agents may also be applied to pathogen-infested crop stubble in order to reduce the inoculum available to infect a subsequent crop, especially under conservation tillage agriculture. Other suitable application procedures can be envisioned by those skilled in the art. Once treated with the biocontrol agents of the present invention, the seeds can be planted in natural or artificial soil and cultivated using conventional procedures to produce plants. After plants have been propagated from seeds treated in accordance with the present invention, the plants may be treated with one or more applications of the biocontrol agents of the present invention to impart disease protection to plants and/or to enhance plant growth.

The biocontrol agents can be applied to plants or plant seeds in accordance with the present invention alone or in a mixture with other materials. Alternatively, the biocontrol agent can be applied separately to plants with other materials being applied at different times.

A composition suitable for treating plants or plant seeds in accordance with the present invention contains a biocontrol agent in a carrier. Suitable carriers include water, aqueous solutions, slurries, solids (e.g., peat, wheat, bran, vermiculite, and pasteurized soil) or dry powders. In this embodiment, the composition contains $10^6$ to $10^8$, preferably $10^7$, colony forming units of the biocontrol agent per milliliter of carrier.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the biocontrol agent can be applied to plant seeds with other conventional seed formulation and treatment materials, including clays and polysaccharides.

EXAMPLES

Example 1

Characterization of the *Bacillus subtilis* Isolate TrigoCor 1448 (ATCC Accession No. 202152)

The bacterial isolate deposited as ATCC Accession No. 202152 (also referred to as "TrigoCor 1448"), was originally identified as *Paenibacillus macerans* (based on GC-FAME analyses and a database search provided by Microbe Inotech Laboratories, St. Louis, Mo.). However, in February 2001, TrigoCor 1448 was reclassified as *Bacillus subtilis*, based on a Basic Local Alignment Search Tool ("BLAST") search of sequences of the 16S ribosomal RNA (rRNA) gene. A 500 base pair segment of the 16S rRNA of TrigoCor 1448 was sequenced by Microbe Inotech Laboratories (St. Louis, Mo.) and has been identified as *Bacillus subtilis* with 99 percent confidence, based on the sequence similarity with entries in the NCBI's GeneBank nucleotide database. Based on this analysis, 529 out of 532 base pairs of the 16S rRNA gene of TrigoCor 1448 matched those of *Bacillus subtilis* strain TB 11 (used for production of a biopolymer flocculent) sequenced in Korea. There were several close matches with other *B. subtilis* strains and with strains identified only as *Bacillus* sp. Similarity with other bacterial species drops off sharply outside of this group.

Example 2

Ribotyping Analysis of *Bacillus subtilis* Isolate TrigoCor 1448

TrigoCor 1448 was further characterized based on its ribotype. Ribotyping is a diagnostic method used to identify and classify bacteria based on differences in their rRNA genes. This method generates a precise and highly reproducible rRNA "fingerprint" that can be used to classify bacteria and distinguish them beyond the species level. In general, this method involves extracting DNA from a sample bacterial colony of interest and then restricting the DNA into discrete-sized fragments. Thereafter, the DNA is transferred to a membrane and probed with a region of the rRNA operon to reveal the pattern of rRNA genes for the sample. The pattern, also referred to as a ribotype or riboprint pattern, is then recorded, digitized, and stored in a database. The sample's riboprint pattern may then be compared against those of other bacteria. Variations that exist among bacteria in both the position and intensity of the resulting rRNA bands are used to classify and identify the sample bacterium.

The ribotyping analysis of TrigoCor 1448 was performed by the Laboratory for Molecular Typing at Cornell University (Ithaca, N.Y.). An isolated pure colony of TrigoCor 1448 was streaked onto fresh BHI (Brain-Heart Infusion) plates. The plates were streaked in such a manner as to result in heavy bacterial growth in the upper portion of a plate and isolated colonies in the remaining portion of the plate. The BHI plates were then incubated for 18–30 hours at approximately 30° C. After overnight incubation, sterile microcentrifuge tubes were filled with sample buffer (approximately 40 μl). Samples of the TrigoCor 1448 isolate growing in the BHI plates were taken from the BHI plates using a sterile toothpick by touching the toothpick to the lawn of growth on the BHI plates. The toothpicks containing the TrigoCor 1448 samples were then placed into an appropriate microcentrifuge tube, which was then vortexed for a few seconds for mixing. For each sample of TrigoCor 1448, two toothpicks were inserted into each sample tube. After completing this process, approximately 30 μl from each tube was transferred to their appropriate well in a sample carrier. The sample carrier was then placed in a heat treatment station to reduce viability and inactivate nucleases. This process of heating and cooling takes about 30 minutes. Lysing agents were added to each well. Approximately 5 μl of lysing agent A was added to the first well of the sample carrier followed by approximately 5 μl of lysing agent B. This was repeated for all 8 wells in the run. The sample carrier was then transported to a commercially available riboprinter characterization unit and processed by the machine; i.e., the Ribo-Printer® Microbial Characterization System (DuPont Qualicon, Wilmington, Del.).

As described in Table 1 (below), the riboprint pattern for TrigoCor 1448 was determined to have a band intensity curve of 256 individual points. Each of the 256 individual points corresponds to a ribotype band of a specific size (i.e., molecular weight, measured in kilobase pairs ("kbs")), and has been assigned a sequential "pattern number" (i.e., from Pattern Number 1 to Pattern Number 256), based on band size. In addition to molecular weight, each of the 256 ribotype bands has been assigned a relative band intensity value, based on a relative scale ranging from 0 to 255, with a relative band intensity value of 0 denoting the lowest relative band intensity and 255 denoting the highest relative band intensity.

TABLE 1

Summary of Riboprint Pattern Data

| Pattern Number | Relative Band Intensity (Scale = 0 to 255) | Estimated Molecular Weight (in kilobase pairs) |
|---|---|---|
| 1 | 0 | 0.51 |
| 2 | 0 | 0.54 |
| 3 | 0 | 0.58 |
| 4 | 0 | 0.61 |
| 5 | 0 | 0.64 |
| 6 | 0 | 0.67 |
| 7 | 0 | 0.70 |
| 8 | 0 | 0.74 |
| 9 | 0 | 0.77 |
| 10 | 0 | 0.80 |
| 11 | 0 | 0.83 |
| 12 | 0 | 0.86 |
| 13 | 0 | 0.89 |
| 14 | 1 | 0.93 |
| 15 | 2 | 0.96 |
| 16 | 2 | 0.99 |
| 17 | 3 | 1.02 |
| 18 | 3 | 1.05 |
| 19 | 3 | 1.09 |
| 20 | 3 | 1.12 |
| 21 | 2 | 1.15 |
| 22 | 1 | 1.18 |
| 23 | 1 | 1.21 |
| 24 | 0 | 1.25 |
| 25 | 0 | 1.28 |
| 26 | 0 | 1.31 |
| 27 | 0 | 1.34 |
| 28 | 0 | 1.37 |
| 29 | 0 | 1.40 |
| 30 | 0 | 1.44 |
| 31 | 0 | 1.47 |
| 32 | 0 | 1.50 |
| 33 | 0 | 1.53 |
| 34 | 0 | 1.56 |
| 35 | 0 | 1.60 |
| 36 | 0 | 1.63 |
| 37 | 0 | 1.66 |
| 38 | 0 | 1.69 |
| 39 | 0 | 1.72 |
| 40 | 0 | 1.75 |
| 41 | 0 | 1.79 |
| 42 | 0 | 1.82 |
| 43 | 0 | 1.85 |
| 44 | 0 | 1.88 |
| 45 | 2 | 1.91 |
| 46 | 7 | 1.95 |
| 47 | 17 | 1.98 |
| 48 | 53 | 2.01 |
| 49 | 105 | 2.04 |
| 50 | 175 | 2.07 |
| 51 | 227 | 2.11 |
| 52 | 254 | 2.14 |
| 53 | 255 | 2.17 |
| 54 | 227 | 2.20 |
| 55 | 200 | 2.24 |
| 56 | 173 | 2.28 |
| 57 | 146 | 2.32 |
| 58 | 115 | 2.36 |
| 59 | 85 | 2.40 |
| 60 | 57 | 2.44 |
| 61 | 37 | 2.48 |
| 62 | 22 | 2.52 |
| 63 | 13 | 2.56 |
| 64 | 8 | 2.60 |
| 65 | 4 | 2.64 |
| 66 | 1 | 2.68 |
| 67 | 0 | 2.72 |
| 68 | 0 | 2.76 |
| 69 | 0 | 2.80 |
| 70 | 2 | 2.84 |
| 71 | 5 | 2.88 |
| 72 | 6 | 2.92 |
| 73 | 6 | 2.96 |
| 74 | 5 | 3.00 |
| 75 | 2 | 3.04 |
| 76 | 0 | 3.08 |
| 77 | 0 | 3.12 |
| 78 | 0 | 3.16 |
| 79 | 0 | 3.20 |
| 80 | 5 | 3.26 |
| 81 | 7 | 3.32 |
| 82 | 8 | 3.37 |
| 83 | 5 | 3.43 |
| 84 | 3 | 3.49 |
| 85 | 1 | 3.54 |
| 86 | 0 | 3.60 |
| 87 | 0 | 3.66 |
| 88 | 0 | 3.72 |

TABLE 1-continued

Summary of Riboprint Pattern Data

| Pattern Number | Relative Band Intensity (Scale = 0 to 255) | Estimated Molecular Weight (in kilobase pairs) |
|---|---|---|
| 89 | 3 | 3.77 |
| 90 | 18 | 3.83 |
| 91 | 47 | 3.89 |
| 92 | 91 | 3.95 |
| 93 | 148 | 4.00 |
| 94 | 189 | 4.06 |
| 95 | 210 | 4.12 |
| 96 | 190 | 4.18 |
| 97 | 155 | 4.23 |
| 98 | 116 | 4.29 |
| 99 | 83 | 4.35 |
| 100 | 61 | 4.41 |
| 101 | 44 | 4.46 |
| 102 | 31 | 4.52 |
| 103 | 22 | 4.58 |
| 104 | 15 | 4.64 |
| 105 | 9 | 4.69 |
| 106 | 5 | 4.75 |
| 107 | 2 | 4.81 |
| 108 | 0 | 4.87 |
| 109 | 0 | 4.92 |
| 110 | 0 | 4.98 |
| 111 | 0 | 5.04 |
| 112 | 0 | 5.09 |
| 113 | 0 | 5.15 |
| 114 | 0 | 5.21 |
| 115 | 0 | 5.27 |
| 116 | 0 | 5.32 |
| 117 | 0 | 5.38 |
| 118 | 21 | 5.44 |
| 119 | 52 | 5.50 |
| 120 | 75 | 5.55 |
| 121 | 90 | 5.61 |
| 122 | 83 | 5.67 |
| 123 | 72 | 5.73 |
| 124 | 62 | 5.78 |
| 125 | 70 | 5.84 |
| 126 | 90 | 5.90 |
| 127 | 114 | 5.96 |
| 128 | 133 | 6.01 |
| 129 | 141 | 6.07 |
| 130 | 145 | 6.13 |
| 131 | 144 | 6.19 |
| 132 | 145 | 6.24 |
| 133 | 144 | 6.30 |
| 134 | 139 | 6.38 |
| 135 | 121 | 6.47 |
| 136 | 95 | 6.55 |
| 137 | 64 | 6.63 |
| 138 | 37 | 6.71 |
| 139 | 18 | 6.80 |
| 140 | 5 | 6.88 |
| 141 | 0 | 6.96 |
| 142 | 0 | 7.04 |
| 143 | 0 | 7.13 |
| 144 | 0 | 7.21 |
| 145 | 0 | 7.29 |
| 146 | 0 | 7.37 |
| 147 | 0 | 7.46 |
| 148 | 0 | 7.54 |
| 149 | 0 | 7.62 |
| 150 | 0 | 7.70 |
| 151 | 0 | 7.79 |
| 152 | 0 | 7.87 |
| 153 | 0 | 7.95 |
| 154 | 0 | 8.03 |
| 155 | 2 | 8.12 |
| 156 | 17 | 8.20 |
| 157 | 42 | 8.28 |
| 158 | 74 | 8.36 |
| 159 | 100 | 8.45 |
| 160 | 105 | 8.53 |
| 161 | 94 | 8.61 |
| 162 | 65 | 8.70 |
| 163 | 39 | 8.78 |
| 164 | 18 | 8.86 |
| 165 | 10 | 8.94 |
| 166 | 5 | 9.02 |
| 167 | 2 | 9.11 |
| 168 | 1 | 9.19 |
| 169 | 0 | 9.27 |
| 170 | 0 | 9.35 |
| 171 | 0 | 9.44 |
| 172 | 0 | 9.52 |
| 173 | 0 | 9.60 |
| 174 | 0 | 9.68 |
| 175 | 0 | 9.77 |
| 176 | 0 | 9.85 |
| 177 | 0 | 9.94 |
| 178 | 0 | 10.02 |
| 179 | 0 | 10.11 |
| 180 | 0 | 10.19 |
| 181 | 0 | 10.27 |
| 182 | 0 | 10.35 |
| 183 | 0 | 10.44 |
| 184 | 0 | 10.52 |
| 185 | 0 | 10.62 |
| 186 | 0 | 10.73 |
| 187 | 0 | 10.83 |
| 188 | 0 | 10.93 |
| 189 | 5 | 11.04 |
| 190 | 17 | 11.14 |
| 191 | 41 | 11.24 |
| 192 | 68 | 11.36 |
| 193 | 92 | 11.47 |
| 194 | 98 | 11.59 |
| 195 | 86 | 11.71 |
| 196 | 65 | 11.83 |
| 197 | 41 | 11.94 |
| 198 | 25 | 12.06 |
| 199 | 14 | 12.18 |
| 200 | 10 | 12.30 |
| 201 | 7 | 12.43 |
| 202 | 5 | 12.56 |
| 203 | 3 | 12.69 |
| 204 | 1 | 12.82 |
| 205 | 0 | 12.95 |
| 206 | 0 | 13.08 |
| 207 | 0 | 13.21 |
| 208 | 0 | 13.37 |
| 209 | 0 | 13.57 |
| 210 | 0 | 13.77 |
| 211 | 0 | 13.97 |
| 212 | 0 | 14.16 |
| 213 | 0 | 14.36 |
| 214 | 0 | 14.56 |
| 215 | 0 | 14.76 |
| 216 | 0 | 14.97 |
| 217 | 0 | 15.18 |
| 218 | 0 | 15.40 |
| 219 | 0 | 15.62 |
| 220 | 0 | 15.84 |
| 221 | 0 | 16.05 |
| 222 | 0 | 16.27 |
| 223 | 0 | 16.54 |
| 224 | 0 | 16.86 |
| 225 | 0 | 17.18 |
| 226 | 0 | 17.50 |
| 227 | 0 | 17.82 |
| 228 | 0 | 18.14 |
| 229 | 0 | 18.46 |
| 230 | 0 | 18.78 |
| 231 | 0 | 21.70 |
| 232 | 0 | 24.62 |
| 233 | 0 | 27.55 |
| 234 | 0 | 30.47 |

TABLE 1-continued

Summary of Riboprint Pattern Data

| Pattern Number | Relative Band Intensity (Scale = 0 to 255) | Estimated Molecular Weight (in kilobase pairs) |
|---|---|---|
| 235 | 0 | 33.39 |
| 236 | 0 | 36.31 |
| 237 | 0 | 39.23 |
| 238 | 0 | 42.16 |
| 239 | 0 | 45.08 |
| 240 | 0 | 48.00 |
| 241 | 0 | 50.92 |
| 242 | 0 | 53.84 |
| 243 | 0 | 56.77 |
| 244 | 0 | 59.69 |
| 245 | 0 | 62.61 |
| 246 | 0 | 65.53 |
| 247 | 0 | 68.45 |
| 248 | 0 | 71.38 |
| 249 | 0 | 74.30 |
| 250 | 0 | 77.22 |
| 251 | 0 | 80.14 |
| 252 | 0 | 83.06 |
| 253 | 0 | 85.99 |
| 254 | 0 | 88.91 |
| 255 | 0 | 91.83 |
| 256 | 0 | 94.75 |

A graphical representation of the riboprint pattern for TrigoCor 1448 revealed seven distinguishable ribotype band peaks, based on band intensity. As summarized in Table 2, the highest point of each of these seven peaks, in order of ascending molecular weight, are represented by Pattern Numbers 53, 95, 121, 130, 132, 160, and 194.

TABLE 2

Summary of the Highest Point of the Seven Band Intensity Peaks

| Pattern Number | Relative Band Intensity (Scale = 0 to 255) | Estimated Molecular Weight (in kilobase pairs) |
|---|---|---|
| 53 | 255 | 2.17 |
| 95 | 210 | 4.12 |
| 121 | 90 | 5.61 |
| 130 | 145 | 6.13 |
| 132 | 145 | 6.24 |
| 160 | 105 | 8.53 |
| 194 | 98 | 11.59 |

Based on the results of the ribotyping analysis, the riboprint pattern for TrigoCor 1448, designated as "#116-752-1 B. Sub," corroborated the identification of TrigoCor 1448 as an isolate of *Bacillus subtilis*. Further, TrigoCor 1448 was shown to have a unique ribotype. The TrigoCor 1448 ribotype differed in position and intensity of rRNA bands as compared to the 34 patterns for *Bacillus subtilis* isolates in the DuPont/Qualicon database used for comparison. The DuPont/Qualicon database for *Bacillus subtilis* included a diverse collection of isolates of industrial interest, environmental isolates, and isolates from culture depositories. The isolate in the Qualicon database with the closest riboprint pattern to TrigoCor 1448 was DUP-12567 from a German culture depository where it is cataloged as DSMZ 8564. However, the riboprint of TrigoCor 1448 was still distinguishable from that of DSMZ 8564, based on the positional and intensity differences between the riboprint patterns of the two isolates.

Example 3

In-vitro Assays for Antibiosis of *F. graminearum* by Bioprotectants

In paired treatments, the radial growth (mm) of *F. graminearum* in the presence or absence of *Bacillus subtilis* isolated TrigoCor 1448 (ATCC Accession No. 202152), *Pseudomonas putida* (ATCC Accession No. 202153), or *Sporobolomyces roseus* (ATCC Accession No. 74456) was measured as a means of ascertaining the antibiosis of the pathogen by candidate bioprotectants. Each bacterial or yeast isolate was transferred onto ¼ strength potato dextrose agar (i.e. PDA) in a circular pattern by means of a small sterile glass funnel. After 2 days of incubation at ambient temperature, an agar disk containing mycelia of the pathogen was transferred into the center of the ring-shaped colony of the bioprotectant or, in the control treatment, onto an uninoculated media plate. The radial growth of the pathogen was measured after 5 days of incubation. There was a minimum of four replicates per treatment.

Example 4

Effect of Bioprotectants on the Infection of *F. moniliforme*-infested Maize Seed Maize seed naturally infected with *F. moniliforme* and treated with *Bacillus subtilis* and *Pseudomonas putida* were assayed for pathogen recovery. One hundred seeds were placed on culture dishes filled with 25% PDA (10 seeds/dish). The plates were rated for the presence of the pathogen after incubation for 5 days under fluorescent lights at ambient temperature. There were four replicates per treatment.

Example 5

Effect of Bioprotectants on the Emergence of Maize Seed Planted in Soil Infested with *F. graminearum*

Maize seed treated with *Bacillus subtilis* and *Pseudomonas putida* was planted in autoclaved greenhouse soil (Metro Mix) mixed 9:1 by volume with autoclaved, *F. graminearum*-inoculated oat kernels. There were four replicates of 100 seeds (10 seeds per pot) per treatment. All treatments were rated for % emergence 21 days after planting.

Example 6

Effect of Seed-Applied Bioprotectants on the Emergence of *F. graminearum*-infected Wheat Seeds Wheat, cultivar NY Batavia, naturally infected with *F. graminearum*, was treated with slurries of *Bacillus subtilis* and *Pseudomonas putida* and then planted in greenhouse soil (Metro Mix). There were four replicates of 100 seeds (10 seeds per pot) per treatment. All treatments were rated for % germination 21 days after planting.

Example 7

Effect of Seed-Applied Bioprotectants on Emergence of Wheat Planted in *F. graminearum*-infested Soil Wheat seed treated with slurries of *Bacillus subtilis*, *Pseudomonas putida*, or thiabendazole (Gustafson LSP 0.25 fl. oz. per 100 lb. seed) was planted in greenhouse soil (Metro Mix). There were four replicates per treatment. All treatments were rated for % germination 7 days after planting.

As shown below in Table 3, *Bacillus subtilis* and *P. putida*, but not the *S. roseus* treatment, were shown to reduce significantly the radial growth of *F. graminearum* in vitro.

TABLE 3

Effect of Bioprotectants on the Growth of *Fusarium graminearum* and *F. moniliforme* in Culture.

| Treatment | Mean Reduction in Radial Growth (mm) Relative to the Nontreated Control | |
|---|---|---|
| | *F. graminearum* | *F. moniliforme* |
| *Bacillus subtilis* | −13.4 | −20.5 |
| *Pseudomonas putida* | −15.2 | −6.5 |
| *Sporobolomyces roseus* | −3.4 | — |

As shown below in Table 4, all treatments reduced significantly the recovery of *F. moniliforme* from naturally infected maize seed. *Bacillus subtilis* gave the greatest control. In this table, means within a column are significantly different (at P=0.05) from each other if they are followed by different letters, according to Duncan's multiple range test of significance. Little, et al., *Agriculture Experimentation*, p. 350 (1978), which is hereby incorporated by reference.

TABLE 4

Effect of Bioprotectants on the Growth of *F. moniliforme* from Naturally Infested Maize Seed.

| Treatment | % Recovery on PDA |
|---|---|
| Non-treated | 35 a |
| *Bacillus subtilis* | 13 d |
| *Pseudomonas putida* | 18 c |

As shown in Table 5, all treatments resulted in significantly greater emergence than the nontreated control. In this table, means within a column are significantly different (at P=0.05) from each other if they are followed by different letters, according to Duncan's multiple range test of significance.

TABLE 5

Effect of Seed-applied Bioprotectants on the Emergence Maize Planted in *F. gramineaurm*-infested Soil.

| Treatment | Mean % emergence |
|---|---|
| Non-treated | 62 d |
| *Bacillus subtilis* | 86 a |
| *Pseudomonas putida* | 83 ab |

*Bacillus subtilis* and *Pseudomonas putida* treatments resulted in significantly greater emergence than the nontreated control, as shown in Table 6. In this table, means within a column are significantly different (at P=0.05) from each other if they are followed by different letters, according to Duncan's multiple range test of significance.

TABLE 6

Effect of Seed-applied Bioprotectants on the Emergence *F. graminearum*-infected Wheat Seeds Planted in Soil.

| Treatment | % Emergence |
|---|---|
| Non-treated | 63 c |
| Bacillus subtilis | 72 a |
| *Pseudomonas putida* | 69 ab |

As shown in Table 7, all treatments resulted in significantly greater emergence than the nontreated control. *Bacillus subtilis* gave the greatest % emergence after the thiabendazole treatment. In this table, means within a column are significantly different (at P=0.05) from each other if they are followed by different letters, according to Duncan's multiple range test of significance.

TABLE 7

Effect of Seed-applied Bioprotectants on the Emergence of Wheat Seeds Planted in *F. graminearum*-infested Soil.

| Treatment | % Germination |
|---|---|
| Non-treated | 50 e |
| *Bacillus subtilis* | 76 b |
| *Pseudomonas putida* | 69 d |
| Thiabendazole | 80 a |

All bioprotectants tested showed some control of seed rot and seedling blight caused by *Fusarium graminearum* or *F. moniliforme*. The spore-forming bacterium, *Bacillus subtilis*, showed the greatest promise as a bioprotectant against seedborne and soilborne *Fursarium* species.

Example 8

Bioprotection of Wheat

Seeds of wheat cultivar Embrapa 24 infected by *Pyrenophora tritici-repentis* were obtained from the basic seed production service, Embrapa, Passo Fundo, RS, Brazil. The following bacterial and fungal bioprotectants were applied to seed: *Bacillus subtilis* and *Pseudomonas putida* biotype B. Iprodione plus thiram-treated and nontreated seeds were used as controls. Colonies of each bacterium were grown on ¼ potato dextrose agar (i.e. PDA) for 24 hr at 24±2° C. Bacterial cells were removed from the surface of the culture medium with a brush and placed in sterile distilled water. The concentration of each bacterium was approximately $10^6$ CFU/ml. A suspension was then applied by dipping the seeds for 3 min., and allowing them to dry at room temperature for 24 hr. The fungicide mixture was tested at a dosage of 150 g Rovrin WP per 100 kg of seeds. Nontreated seeds were soaked in sterile distilled water, for 3 min, and allowed to dry in the same manner as microbial-treated seeds. For the laboratory experiment, each treatment was replicated four times (each replicate 100 grains, 10 grains per plate) and placed under black light under a photoperiod of 12 hr at 24±2° C. The experimental arrangement was a completely randomized design. The presence of *P. tritici-repentis* was determined 5 days after plating. The data were expressed as percentage of seeds from which the pathogen was recovered. An experiment was done to evaluate the incidence of transmission in a highly infected seed lot. Transmission was scored as the percentage of seedlings with characteristic coleoptile lesions.

Radial growth in the laboratory test was measured using the funnel method (Luz, W. C., "Controle biológico das doencas na espermosfera," *Controle biológico de doencas de plantas*, EMBRAPA-CNPDA, Jaguari na, Brasil pages 25–31 (1991), which is hereby incorporated by reference).

For the field experiment, seeds with each treatment were manually sown in plots of 12 rows, 3 m long. The space between rows was 20 cm and the amount of seeds was equivalent to 120 kg per ha. Treated plots in each experiment were arranged in a randomized block design. Emergence was measured 21 days after sowing. At maturity, eight central rows of each plot were harvested and the yield was determined as kg/ha. The data were subjected to analysis of variance and the means separated by Duncan's multiple range test (P=0.05).

Both bioprotectant bacteria inhibited strongly the radial growth of *P. tritici-repentis* and its recovery from infected seed (Table 8). Treatments with *Bacillus subtilis* and *Pseudomonas putida* biotype B, inhibited completely the transmission of *P. tritici-repentis* to seedlings (Table 8).

TABLE 8

Effect of Bioprotectants on Radial Growth, Recovery from Infected Seeds, and Percent Seed Transmission of *Pyrenophora tritici-repentis*.

| Treatments | Radial growth (cm) | % recovery from seeds lot I | % recovery from seeds lot II | % transmission lot I |
|---|---|---|---|---|
| Nontreated | 2.5 | 62 | 22 | 16 |
| *Bacillus subtilis* | 0.0 | 0 | 0 | 0 |
| *Pseudomonas putida* biotype B | 0.2 | 0 | 0 | 0 |
| Iprodione + thiram Rovrin WP | — | 0 | 0 | 0 |

Seeds were also naturally infected, but at a lower incidence, by *Fusarium graminearum* Schwabe and *Bipolaris sorokinianum* (Sacc.) Shoem.; the two bacteria also inhibited recovery of these pathogens from seed.

Data from the field experiment are shown in Table 9.

TABLE 9

Effect of Seed-applied Bioprotectants on Seedling Emergence and Yield of Wheat in the Field

| Treatments | Seedling emergence | Yield (kg/ha) |
|---|---|---|
| Nontreated | 311 c | 1666 c |
| *Bacillus subtilis* | 326 a | 2201 a |
| *Pseudomonas putida* biotype B | 336 a | 2112 a |
| Iprodione + thiram Rovrin WP | 330 a | 2110 a |

All biological or chemical treatments significantly increased seedling emergence of wheat over that in the nonprotected plots. *Bacillus subtilis* and *Psedomonas putida* biotype B provided the greatest yield increase over that of nonprotected plots (Table 9).

The beneficial effects of plant growth promoting and bioprotecting rhizobacteria (i.e. PGPBR) on plants have been reviewed (Bakker et al., "Suppression of Soil-Borne Plant Pathogens by Fluorescent Pseudomonads: Mechanisms and Prospects," *Biotic Interactions and Soil Borne Diseases*, Ed. A. B. R. Beemster, et al., pp. 217–23, Amsterdam, The Netherlands, Elsevier (1991); Kloepper, J. W. "Plant Growth-Promoting Rhizobacteria as Biological Control Agents of Soilborne Diseases," *The Biological Control of Plant Diseases*, pp. 142–52 (1991); Luz, W. C., "Microbiolizacão de sementes para o controle de doencas das plantas," *Revisão Annual de Patologia de Plantas*, Passo Fundo, Brasil, W. C. da Luz, J. M. C. Fernandes, A. M. Prestes and E. C. Picinini, ed., pages 35–77 (1993); Luz, W. C., "Rizobabactérias promotoras de crescimento de plantas e de bioprotecão," *Revisão Annual de Patologia de Plantas*, Passo Fundo, Brasil, W. C. da Luz, J. M. C. Fernandes, A. M. Prestes and E. C. Picinini, ed., pages 1–49 (1996), which are hereby incorporated by reference), as having the benefits of fungal bioprotectants (Harman, G. E., "Seed Treatments for Biological Control of Plant Disease," *Crop. Prot.*, 10:166–71 (1991), which is hereby incorporated by reference). Microbial agents used as bioprotectants and yield stimulants will be a significant tactic of disease management in the next century (Luz, W. C. da RizababactÈrias promotoras de crescimento de plantas e de bioproteÁ,o. Pages 1–49 in W. C. da Luz, J. M. C. Fernandes, A. M. Prestes and E. C. Picinini, ed., *Revis,,o Anual de Patologia de Plantas.*, Passo Fundo, Brasi (1996), which are hereby incorporated by reference). The two PGPBRs reported here show great promise as yield stimulators and bioprotectants of wheat against diseases.

Example 9

Biocontrol of Wheat Scab with Microbial Antagonists

Plants of spring wheat ND594 were grown in a glasshouse at Cornell University, Ithaca, N.Y. At mid-anthesis stage, spikes of plants were either sprayed with water or with cell suspensions of potential bioprotectant microorganisms. All spikes were challenge-inoculated 24 hr later with a *F. graminearum* spore suspension, and the plants were incubated overnight at high relative humidity. Thereafter, the plants were allowed to grow on a glasshouse bench under ambient conditions through grain maturation. Harvested spikes were evaluated for incidence of seeds infected by *Fursarium*, 100-kernel weight, and deoxynivalenol (DON) content. *Fusarium* infection was determined by characteristic growth of the pathogen from seed incubated on blotters after commencement of germination followed by freezing to kill the seed embryos. DON was analyzed by high pressure liquid chromatagraphy at the Cornell Veterinary Diagnostic Laboratory.

*Bacillus subtilis* (Embrapa-Trigo), *Pseudomonas putida* biotype B (Embrapa-Trigo), and *Sporobolomyces roseus* (Embrapa-Trigo) consistently protected spikes and resulted in average (three experiments) increases in kernel weight over those of nonprotected spikes. Table 10 shows the protection of wheat grains by microbial strains against weight reduction, *Fursarium* infection, and contamination by the *Fursarium* mycotoxin, deoxynivalenol. (Means of four replicates with standard errors in parentheses; results of one of three experiments shown).

TABLE 10

| Inoculation 1 | Inoculation 2 | Grain weight (g/100 seeds) | Incidence of Fusarium (%) | Deoxynivalenol contamination (ppm) |
|---|---|---|---|---|
| Water | Water | 2.86 (0.37) | 0 (0.0) | 0.16 (0.16) |
| Water | Fusarium | 2.06 (0.54) | 34 (6.2) | 10.70 (8.02) |

TABLE 10-continued

| Inoculation 1 | Inoculation 2 | Grain weight (g/100 seeds) | Incidence of Fusarium (%) | Deoxyni-valenol contami-nation (ppm) |
|---|---|---|---|---|
| *Sporobolomyces roseus* | Fusarium | 2.08 (0.53) | 25 (12.8) | (2.73) |
| *Pseudomonas putida* | Fusarium | 2.52 (0.54) | 17 (8.5) | (1.23) |
| *Bacillus subtilis* | Fusarium | 2.75 (0.14) | 15 (14.2) | (0.86) |

Example 10

Inhibition of Mycelial Growth (Antibiosis) of Fungal Pathogens of Cereals by *Bacillus subtilis* Isolate 144 from Brazil One indication that a microorganism strain may be useful for biocontrol of fungal plant pathogens is its ability to inhibit mycelial (filamentous) growth of fungi in vitro. *Bacillus subtilis* isolate 144, a spore-forming bacterium isolated from roots of wheat plants in Brazil, was tested for antibiosis in vitro against a broad range of economically important fungal pathogens of wheat and corn.

In paired treatments, in the presence or absence of *Bacillus subtilis* isolate 144, the radial growth (mm) of fungal pathogens was measured as a means of estimating antibiosis. Bacterial cells were transferred onto a Petri dish of ¼ strength potato dextrose agar by means of a small glass funnel. After two days incubation at room temperature, an agar disk containing mycelia of the fungus was transferred into the center of the ring-shaped colony of the bioprotectant or, in the nontreated, onto an uninoculated media plate. The radial growth was measured after 5 days. There were a minimum of four replicates per experiment.

*Bacillus subtilis* isolate 144 strongly inhibited the mycelial growth of several cereal pathogens in vitro (Table 11). This indicates the production of antibiotic(s) active against a broad range of plant pathogenic fungi. Antibiosis is a useful trait for a plant disease biocontrol strain. The antibiotic(s) may also find direct uses as antimycotics in agriculture or medicine.

TABLE 11

In vitro Inhibition by *Bacillus subtilis* Isolate 144 of Mycelial Growth of Fungi Pathogenic to Cereals

|  | Radial Growth of Mycelium (mm) | |
|---|---|---|
| Plant pathogenic fungus: (plant disease) | Fungus alone | Fungus in presence of *B. subtilis* |
| *Cochliobolus sativus* (spot blotch of wheat) | 23 a* | 2 b |
| *Pyrenophora tritici-repentis* (tan spot of wheat) | 25 a | 0.5 b |
| *Stagonospora nodorum* (*S. nodorum* blotch of wheat) | 5 a | 1 b |
| *Stagonospora avenae* f. sp. *triticea* (*S. avenae* blotch of wheat | 12 a | 1 b |
| *Colletotrichum graminicola* (anthracnose of corn) | 25 a | 2 b |
| *Stenocarpella maydis* (Stenocarpella ear and stalk rot of corn) | 21 a | 2 b |
| *Stenocarpela macrospora* (Stenocarpella ear and stalk rot of corn) | 40 a | 5 b |

TABLE 11-continued

In vitro Inhibition by *Bacillus subtilis* Isolate 144 of Mycelial Growth of Fungi Pathogenic to Cereals

|  | Radial Growth of Mycelium (mm) | |
|---|---|---|
| Plant pathogenic fungus: (plant disease) | Fungus alone | Fungus in presence of *B. subtilis* |
| *Fusarium moniliforme* (Fusarium ear and stalk rot of corn) | 36 a | 7 b |
| *Fusarium graminearum* (wheat scab; and Gibberella ear and stalk rot of corn) | 24 a 14 a | 11 b 7 b |

*Means within a row (same fungus) and following by different letters differ significantly according to the protected Duncan's multiple range test.

Example 11

Control of Seedborne Cereal Diseases by Seed Treatment with Microbial Antagonists Microbial bioprotectants may provide a safe and effective alternative or complement to chemical fungicides for control of seedborne fungal pathogens in cereals and other crop plants.

Seed lots of wheat and corn naturally infected by pathogenic fungi were located and used for testing the efficacy of seed-applied bioprotectants. Seeds were either soaked in water or cell suspensions of *Bacillus subtilis* isolate 144 or *Pseudomonas putida* biotype B isolate 63, then allowed to dry briefly before incubation on moist blotter papers (for isolation of fungi) or sowing in soil. Seedlings were scored for percentage emergence and pathogen transmission (based on coleoptile lesions).

*Bacillus subtilis* isolate 144 and *Pseudomonas putida* biotype B isolate 63 applied to fungal-infected seeds of corn and wheat each resulted in significantly less seedborne inoculum and less seed-to-seedling disease transmission of several fungal pathogens (Table 12). They also resulted in increased emergence of infected seedlings in soil. Both show considerable potential as biological seed protectants for cereal seeds.

TABLE 12

Biocontrol of Seedborne Fungal Pathogens of Cereals as Measured by Decreased Recovery of Fungi from Seed, Decreased Transmission of Fungi to Seedlings, and Increased Seedling Emergence.

|  | Seed treatment | | |
|---|---|---|---|
| Seedborne fungus: | Non-treated | *Bacillus subtilis* 144 | *Pseudomonas putida* 63 |
|  | Isolation from seeds (%) | | |
| *Cochliobolus sativus* (wheat seed) | 18 a* | 0 c | 2 b |
| *Fusarium moniliforme* (corn seed) | 35 a | 13 c | 18 b |
|  | Transmission to seedlings (%) | | |
| *Cochliobolus sativus* (wheat seed in field soil) | 46 a | 7 c | 12 b |
| *Cochliobolus sativus* (wheat seed in autoclaved soil) | 57 a | 10 c | 17 b |
| *Stagonospora nodorum* (wheat seed in soil) | 47 a | 15 c | 11 b |

TABLE 12-continued

Biocontrol of Seedborne Fungal Pathogens of Cereals as Measured by Decreased Recovery of Fungi from Seed, Decreased Transmission of Fungi to Seedlings, and Increased Seedling Emergence.

| Seedborne fungus: | Seed treatment | | |
|---|---|---|---|
| | Non-treated | Bacillus subtilis 144 | Pseudomonas putida 63 |
| | Emergence of seedlings (%) | | |
| Cochliobolus sativus (wheat seed in soil) | 54 b | 70 a | 56 b |
| Fusarium graminearum (wheat seed in soil) | 50 c | 76 a | 69 b |
| Stagonospora nodorum (wheat seed in soil) | 88 c | 94 a | 91 b |

*Means within a row (same seedlot) and followed by different letters differ significantly according to the protected Duncan's multiple range test.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated *Bacillus subtilis* having ATCC Accession No. 202152.

2. A composition comprising:
an isolated *Bacillus subtilis* according to claim 1 and a carrier.

3. A composition according to claim 2 further comprising a fertilizer, insecticide, fungicide, nematacide, or mixtures thereof.

4. A composition according to claim 2 further comprising buffering agents, wetting agents, coating agents, abrading agents, clay, polysaccharides, or mixtures thereof.

5. A method of protecting plants against plant pathogens comprising:
applying to plants, plants seeds, or soil surrounding plants or plant seeds a biocontrol agent comprising an isolated *Bacillus subtilis* according to claim 1 under conditions effective to protect said plants or the plants produced from said plant seeds against said plant pathogens.

6. The method according to claim 5, wherein the biocontrol agent is used to treat plants by topical application.

7. The method according to claim 5, wherein the biocontrol agent is used to treat plant seeds by topical application, said method further comprising:
growing plants from said seeds topically treated with the biocontrol agent.

8. The method according to claim 5, wherein the biocontrol agent is used to treat soil around the plants.

9. The method according to claim 5, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

10. The method according to claim 5, wherein the plant is selected from the group consisting of *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

11. A method of enhancing plant growth comprising:
applying to plants, plants seeds, or soil surrounding plants a biocontrol agent comprising an isolated *Bacillus subtilis* according to claim 1 under conditions effective to enhance growth in said plants or in the plants produced from said plant seeds.

12. The method according to claim 11, wherein the biocontrol agent is used to treat plant seeds by topical application, said method further comprising:
growing plants from said seeds topically treated with the biocontrol agent.

13. The method according to claim 11, wherein the biocontrol agent is used to treat soil around the plants.

14. The method according to claim 11, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

15. The method according to claim 11, wherein the plant is selected from the group consisting of *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

16. An isolated *Bacillus subtilis* having ATCC Accession No. 202152 and having a distinctive ribotype pattern, said ribotype pattern comprising:
a first peak having a relative band intensity ("RBI") of between about 204 and 306 and an estimated molecular weight of between about 1.70 and 2.70 kilobase pairs (kb);
a second peak having an RBI of between about 168 and 252 and a molecular weight of between about 3.60 and 4.60 kb;
a third peak having an RBI of between about 72 and 108 and a molecular weight of between about 5.10 and 6.10 kb;
a fourth peak having an RBI of between about 116 and 174 and a molecular weight of between about 5.60 and 6.60 kb;
a fifth peak having an RBI of between about 116 and 174 and a molecular weight of between about 5.70 and 6.70 kb;
a sixth peak having an RBI of between about 84 and 126 and a molecular weight of between about 8.00 and 9.00 kb; and
a seventh peak having an RBI of between about 78 and 118 and a molecular weight of between about 11.00 and 12.17 kb,
and wherein said RBI is a value on a scale from 0 to 255.

17. The isolated *Bacillus subtilis* according to claim 16, wherein said ribotype pattern comprises:
a first peak having an RBI of approximately 255 and an estimated molecular weight of approximately 2.17 kb;
a second peak having an RBI of approximately 210 and a molecular weight of approximately 4.12 kb;
a third peak having an RBI of approximately 90 and a molecular weight of approximately 5.61 kb;
a fourth peak having an RBI of approximately 145 and a molecular weight of approximately 6.13 kb;
a fifth peak having an RBI of approximately 145 and a molecular weight of approximately 6.24 kb;

a sixth peak having an RBI of approximately 105 and a molecular weight of approximately 8.53 kb; and a seventh peak having an RBI of approximately 98 and a molecular weight of approximately 11.59 kb.

18. The isolated *B. subtilis* according to claim 16, wherein the ribotype pattern is substantially similar to that delineated in Table 1 of the present application.

19. A composition comprising:

an isolated *Bacillus subtilis* according to claim 16 and a carrier.

20. A composition according to claim 19 further comprising a fertilizer, insecticide, fungicide, nematacide, or mixtures thereof.

21. A composition according to claim 19 further comprising buffering agents, wetting agents, coating agents, abrading agents, clay, polysaccharides, or mixtures thereof.

22. A method of protecting plants against plant pathogens comprising:

applying to plants, plants seeds, or soil surrounding plants or plant seeds a biocontrol agent comprising an isolated *Bacillus subtilis* according to claim 16 under conditions effective to protect said plants or the plants produced from said plant seeds against said plant pathogens.

23. The method according to claim 22, wherein the biocontrol agent is used to treat plants by topical application.

24. The method according to claim 22, wherein the biocontrol agent is used to treat plant seeds by topical application, said method further comprising:

growing plants from said seeds topically treated with the biocontrol agent.

25. The method according to claim 22, wherein the biocontrol agent is used to treat soil around the plants.

26. The method according to claim 22, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

27. The method according to claim 22, wherein the plant is selected from the group consisting of *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

28. A method of enhancing plant growth comprising:

applying to plants, plants seeds, or soil surrounding plants a biocontrol agent comprising an isolated *Bacillus subtilis* according to claim 16 under conditions effective to enhance growth in said plants or in the plants produced from said plant seeds.

29. The method according to claim 28, wherein the biocontrol agent is used to treat plants by topical application.

30. The method according to claim 28, wherein the biocontrol agent is used to treat plant seeds by topical application, said method further comprising:

growing plants from said seeds topically treated with the biocontrol agent.

31. The method according to claim 28, wherein the biocontrol agent is used to treat soil around the plants.

32. The method according to claim 28, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

33. The method according to claim 28, wherein the plant is selected from the group consisting of *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

\* \* \* \* \*